United States Patent [19]
Alaska et al.

[11] Patent Number: 5,744,587
[45] Date of Patent: Apr. 28, 1998

[54] METHOD FOR PURIFYING THROMBOPOIETIN

[75] Inventors: Andrew R. Alaska; Jin-Jyi Chang, both of Issaquah; William Downey, Seattle; John W. Forstrom, Seattle; Linh Phan, Seattle, all of Wash.

[73] Assignee: ZymoGenetics, Inc., Seattle, Wash.

[21] Appl. No.: 484,246

[22] Filed: Jun. 7, 1995

[51] Int. Cl.$^6$ .......................... A61K 38/24; A61K 38/27; C04K 1/00; C04K 14/00
[52] U.S. Cl. .......................... 530/399; 530/397; 530/412; 435/69.6
[58] Field of Search .......................... 530/399, 397, 530/412; 435/69.6

[56] References Cited

U.S. PATENT DOCUMENTS 5,128,449  7/1992  McDonald .............................. 530/351
5,571,686  11/1996  Rosenberg et al. .......................... 435/29

OTHER PUBLICATIONS

Li et al., Blood 84 (10 Supp. 1): 330a, abstract No. 1307, 1994.
Bartley et al., Cell 77: 1117–1124, 1994.
de Sauvage et al., Nature 369: 533–538, 1994.
McDonald, The American Journal of Pediatric Hematology/Oncology 14(1): 8–21, 1992.
McDonald, Exp. Hematol. 16: 201–205, 1988.
Hill et al., Exp. Hematol. 20: 354–360, 1992.
McDonald, et al., Thrombopoietin From Human Embryonic Kidney Cells Is the Same Factor as c-mpl-Ligand, Blood, 85, pp. 292–294, 1995.
Kuter, et al., The Purification of megapoietin: A physiological regulator of megakaryocyte growth and platelet production. Proc. Natl. Acad. Sci. USA, vool. 91, pp. 11104–11108, Nov. 1994.
McDonald, et al., Current Status of Thrombopoietin, Advances in Experimental Medicine and Biology, vol. 241, pp. 243–253, 1988.
Nagasawa, et al., Thrombopoietic activity of human interleukin–6, FEBS Letters, vol. 260, No. 2, pp. 176–178, Jan. 1990.

Withy, et al., Growth Factors Produced by Human Embryonic Kidney Cells That Influence Megakaryopoiesis Include Erythropoietin, Interleukin 6, and Transformin Growth Factor–Beta, Journal of Cellular Physiology, vol. 153, pp. 362–372, 1992.
McDonald, et al. Studies on the purification of thrombopoietin from kidney cell culture medium, J. Lab. Clin. Med., vol. 106, No. 2, pp. 162–174, Aug. 1985.
McDonald, et al., Recovery of thrombopoietin during purification, Biochemical Medicine and Metabolic Biology, vol. 37, No. 3, pp. 335–343, 1987.
Evatt, et al. Partail purification of thrombopoietin from the plasma of thrombocytopenic rabbits, Blood, vol. 54, No. 2, pp. 377–388, Aug. 1979.
Freifelder, Physical Biochemistry, Second Edition, Chromatography, pp. 260–262 and 268–270, 1982.
Bonnerjea, et al., Protein Purification The Right Step at the Right Time, Biotechnology, vol. 4, pp. 955–958, Nov. 1986.
Sofer, et al., Designing an Optimal Chromatographic Purification Scheme for Proteins, Biotechniques, pp. 198–203, Nov.–Dec. 1983.
Harris, et al., Protein purification methods A practical approach, pp. 238–242, 258–262, 1989.
Hill, et al. Partial purification of thrombopoietin using lectin chromatography, Exp. Heamtol., vol. 14, No. 8, pp. 752–759, Sep. 1986.
Shimada, et al., Production of thrombopoietin (TPO) by rat heaptocytes, Exp. Hematol., vol. 23, No. 13, pp. 1388–1396, 1995.

Primary Examiner—Cecilia J. Tsang
Assistant Examiner—Jennifer Harle
Attorney, Agent, or Firm—Gary E. Parker

[57] ABSTRACT

Methods of removing protein contaminants from a solution comprising thrombopoietin are disclosed. The solution is exposed to hydroxyapatite, whereby protein contaminants are bound to the hydroxyapatite and the thrombopoietin remains substantially unbound, and the unbound thrombopoietin is recovered. The use of hydroxyapatite is advantageously combined with other purification and concentration techniques, including ion-exchange chromatography, ligand affinity chromatography, hydrophobic interaction chromatography, ultrafiltration, and differential precipitation.

19 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 353 amino acids
    ( B ) TYPE: amino acid
    ( D ) TOPOLOGY: linear ( i i ) MOLECULE TYPE: protein ( x i ) SEQUENCE DESCRIPTION: SEQ ID NO:1:

```
Met  Glu  Leu  Thr  Glu  Leu  Leu  Leu  Val  Val  Met  Leu  Leu  Leu  Thr  Ala
  1                  5                      10                         15
Arg  Leu  Thr  Leu  Ser  Ser  Pro  Ala  Pro  Ala  Cys  Asp  Leu  Arg  Val
                20                  25                      30
Leu  Ser  Lys  Leu  Leu  Arg  Asp  Ser  His  Val  Leu  His  Ser  Arg  Leu  Ser
           35                      40                      45
Gln  Cys  Pro  Glu  Val  His  Pro  Leu  Pro  Thr  Pro  Val  Leu  Leu  Pro  Ala
     50                       55                      60
Val  Asp  Phe  Ser  Leu  Gly  Glu  Trp  Lys  Thr  Gln  Met  Glu  Glu  Thr  Lys
 65                       70                  75                          80
Ala  Gln  Asp  Ile  Leu  Gly  Ala  Val  Thr  Leu  Leu  Leu  Glu  Gly  Val  Met
                     85                      90                          95
Ala  Ala  Arg  Gly  Gln  Leu  Gly  Pro  Thr  Cys  Leu  Ser  Ser  Leu  Leu  Gly
               100                      105                     110
Gln  Leu  Ser  Gly  Gln  Val  Arg  Leu  Leu  Leu  Gly  Ala  Leu  Gln  Ser  Leu
          115                      120                     125
Leu  Gly  Thr  Gln  Leu  Pro  Pro  Gln  Gly  Arg  Thr  Thr  Ala  His  Lys  Asp
     130                      135                     140
Pro  Asn  Ala  Ile  Phe  Leu  Ser  Phe  Gln  His  Leu  Leu  Arg  Gly  Lys  Val
145                       150                     155                     160
Arg  Phe  Leu  Met  Leu  Val  Gly  Gly  Ser  Thr  Leu  Cys  Val  Arg  Arg  Ala
               165                      170                     175
Pro  Pro  Thr  Thr  Ala  Val  Pro  Ser  Arg  Thr  Ser  Leu  Val  Leu  Thr  Leu
               180                      185                     190
Asn  Glu  Leu  Pro  Asn  Arg  Thr  Ser  Gly  Leu  Leu  Glu  Thr  Asn  Phe  Thr
          195                      200                     205
Ala  Ser  Ala  Arg  Thr  Thr  Gly  Ser  Gly  Leu  Leu  Lys  Trp  Gln  Gln  Gly
     210                      215                     220
Phe  Arg  Ala  Lys  Ile  Pro  Gly  Leu  Leu  Asn  Gln  Thr  Ser  Arg  Ser  Leu
225                       230                     235                     240
Asp  Gln  Ile  Pro  Gly  Tyr  Leu  Asn  Arg  Ile  His  Glu  Leu  Leu  Asn  Gly
                    245                      250                     255
Thr  Arg  Gly  Leu  Phe  Pro  Gly  Pro  Ser  Arg  Arg  Thr  Leu  Gly  Ala  Pro
               260                      265                     270
Asp  Ile  Ser  Ser  Gly  Thr  Ser  Asp  Thr  Gly  Ser  Leu  Pro  Pro  Asn  Leu
          275                      280                     285
Gln  Pro  Gly  Tyr  Ser  Pro  Ser  Pro  Thr  His  Pro  Pro  Thr  Gly  Gln  Tyr
     290                      295                     300
Thr  Leu  Phe  Pro  Leu  Pro  Pro  Thr  Leu  Pro  Thr  Pro  Val  Val  Gln  Leu
305                       310                     315                     320
His  Pro  Leu  Leu  Pro  Asp  Pro  Ser  Ala  Pro  Thr  Pro  Thr  Pro  Thr  Ser
```

|       |     |     |     |     | 325 |     |     |     |     | 330 |     |     |     |     | 335 |     |     |
|-------|-----|-----|-----|-----|-----|-----|-----|-----|-----|-----|-----|-----|-----|-----|-----|-----|-----|

Pro Leu Leu Asn Thr Ser Tyr Thr His Ser Gln Asn Leu Ser Gln Glu
                340                     345                 350

Gly ( 2 ) INFORMATION FOR SEQ ID NO:2:

( i ) SEQUENCE CHARACTERISTICS:
        ( A ) LENGTH: 379 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met Ala Pro Gly Lys Ile Gln Gly Arg Gly Pro Ile Gln Gly Ala Thr
 1               5                  10                  15

Ser Val Arg His Leu Ala Arg Met Glu Leu Thr Asp Leu Leu Leu Ala
             20                  25                  30

Ala Met Leu Leu Ala Val Ala Arg Leu Thr Leu Ser Ser Pro Val Ala
         35                  40                  45

Pro Ala Cys Asp Pro Arg Leu Leu Asn Lys Leu Leu Arg Asp Ser His
     50                  55                  60

Leu Leu His Ser Arg Leu Ser Gln Cys Pro Asp Val Asp Pro Leu Ser
65                  70                  75                  80

Ile Pro Val Leu Leu Pro Ala Val Asp Phe Ser Leu Gly Glu Trp Lys
                 85                  90                  95

Thr Gln Thr Glu Gln Ser Lys Ala Gln Asp Ile Leu Gly Ala Val Ser
            100                 105                 110

Leu Leu Leu Glu Gly Val Met Ala Ala Arg Gly Gln Leu Glu Pro Ser
        115                 120                 125

Cys Leu Ser Ser Leu Leu Gly Gln Leu Ser Gly Gln Val Arg Leu Leu
    130                 135                 140

Leu Gly Ala Leu Gln Gly Leu Leu Gly Thr Gln Leu Pro Leu Gln Gly
145                 150                 155                 160

Arg Thr Thr Ala His Lys Asp Pro Asn Ala Leu Phe Leu Ser Leu Gln
                165                 170                 175

Gln Leu Leu Arg Gly Lys Val Arg Phe Leu Leu Leu Val Glu Gly Pro
            180                 185                 190

Thr Leu Cys Val Arg Arg Thr Leu Pro Thr Thr Ala Val Pro Ser Ser
        195                 200                 205

Thr Ser Gln Leu Leu Thr Leu Asn Lys Phe Pro Asn Arg Thr Ser Gly
    210                 215                 220

Leu Leu Glu Thr Asn Phe Ser Val Thr Ala Arg Thr Ala Gly Pro Gly
225                 230                 235                 240

Leu Leu Ser Arg Leu Gln Gly Phe Arg Val Lys Ile Thr Pro Gly Gln
                245                 250                 255

Leu Asn Gln Thr Ser Arg Ser Pro Val Gln Ile Ser Gly Tyr Leu Asn
            260                 265                 270

Arg Thr His Gly Pro Val Asn Gly Thr His Gly Leu Phe Ala Gly Thr
        275                 280                 285

Ser Leu Gln Thr Leu Glu Ala Ser Asp Ile Ser Pro Gly Ala Phe Asn
    290                 295                 300

Lys Gly Ser Leu Ala Phe Asn Leu Gln Gly Gly Leu Pro Pro Ser Pro
305                 310                 315                 320

Ser Leu Ala Pro Asp Gly His Thr Pro Phe Pro Pro Ser Pro Ala Leu

|   |   |   | 325 |   |   |   |   | 330 |   |   |   |   | 335 |   |   |
|---|---|---|-----|---|---|---|---|-----|---|---|---|---|-----|---|---|
| Pro | Thr | Thr | His | Gly | Ser | Pro | Pro | Gln | Leu | His | Pro | Leu | Phe | Pro | Asp |
|   |   |   | 340 |   |   |   |   | 345 |   |   |   |   | 350 |   |   |
| Pro | Ser | Thr | Thr | Met | Pro | Asn | Ser | Thr | Ala | Pro | His | Pro | Val | Thr | Met |
|   |   |   355 |   |   |   |   | 360 |   |   |   |   | 365 |   |   |   |
| Tyr | Pro | His | Pro | Arg | Asn | Leu | Ser | Gln | Glu | Thr |   |   |   |   |   |
|   |   370 |   |   |   |   | 375 |   |   |   |   |   |   |   |   |

METHOD FOR PURIFYING THROMBOPOIETIN

BACKGROUND OF THE INVENTION

Hematopoiesis is the process by which blood cells develop and differentiate from pluripotent stem cells in the bone marrow. This process involves a complex interplay of polypeptide growth factors (cytokines) acting via membrane-bound receptors on the target cells. Cytokine action results in cellular proliferation and differentiation, with a response to a particular cytokine often being lineage-specific and/or stage-specific. Development of a single cell type, such as a platelet, from a stem cell may require the coordinated action of a plurality of cytokines acting in the proper sequence.

The known cytokines include the interleukins, such as IL-1, IL-2, IL-3, IL-6, IL-8, etc.; and the colony stimulating factors, such as G-CSF, M-CSF, GM-CSF, erythropoietin (EPO), etc. In general, the interleukins act as mediators of immune and inflammatory responses. The colony stimulating factors stimulate the proliferation of marrow-derived cells, activate mature leukocytes, and otherwise form an integral part of the host's response to inflammatory, infectious, and immunologic challenges.

Various cytokines have been developed as therapeutic agents. For example, erythropoietin, which stimulates the development of erythrocytes, is used in the treatment of anemia arising from renal failure. Several of the colony stimulating factors have been used in conjunction with cancer chemotherapy to speed the recovery of patients' immune systems. Interleukin-2, α-interferon and γ-interferon are used in the treatment of certain cancers.

An activity that stimulates megakaryocytopoiesis and thrombocytopoiesis has been identified in body fluids of thrombocytopenic animals and is referred to in the literature as "thrombopoietin" (recently reviewed by McDonald, *Exp. Hematol.* 16:201–205, 1988 and McDonald, *Am. J. Ped. Hematol. Oncol.* 14:8–21, 1992). Recently, several groups have isolated and/or cloned thrombopoietin (TPO) based on its ability to bind to the cellular mpl receptor and stimulate megakaryocytopoiesis and thrombocytopoiesis. See, de Sauvage et al., *Nature* 369:533–538, 1994; Lok et al., *Nature* 369:565–568, 1994; Kaushansky et al., *Nature* 369:568–571, 1994; Wendling et al., *Nature* 369:571–574, 1994; and Bartley et al., *Cell* 77:1117–1124, 1994.

The amino acid sequences of the primary translation products of human and mouse TPO cDNAs are shown in SEQ ID NO:1 and SEQ ID NO:2, respectively. Analytical and experimental evidence indicates that the mature proteins begin at residue Ser-22 (human) and Ser-45 (mouse). TPO is subject to proteolysis and has been isolated in heterogeneous or degraded form (de Sauvage et al., *Nature* 369:533–538, 1994; Bartley et al., *Cell* 77:1117–1124, 1994). Molecular species as small as 25 kD have been found to be active in vitro (Bartley et al., ibid), and recombinant human TPO amino-terminal polypeptides of 153 (de Sauvage et al., ibid) and 174 amino acids (Bartley et al., ibid) have been reported as being active in vitro, as has the product of expression of the full-length human cDNA (Bartley et al., ibid).

Preparations of thrombopoietin reported in the scientific literature are not well characterized as to composition and the relative activities of the various molecular species, although at least some of the proteolytic products are biologically active. However, little work has been done to date on the large-scale production of thrombopoietin, and there remains a need in the art for methods of producing the protein in large amounts and in a cost-effective manner. In particular, there is a need for methods of purifying thrombopoietin from biological fluids, and for producing it in a form suitable for use in pharmaceutical preparations. There is also a need for methods of preparing thrombopoietin free of contaminant proteins, including fragments and aggregates of TPO. The present invention provides such methods, as well as other, related advantages.

SUMMARY OF THE INVENTION

The present invention provides methods for removing protein contaminants from a solution comprising thrombopoietin and protein contaminants, including aggregates of thrombopoietin. These methods comprise exposing the solution to hydroxyapatite, whereby the protein contaminants are bound to the hydroxyapatite and the thrombopoietin remains substantially unbound, and recovering unbound thrombopoietin. Within one embodiment of the invention, the TPO-containing solution is prepared by fractionating a TPO-containing liquid composition by ion-exchange chromatography, ligand affinity chromatography or hydrophobic interaction chromatography. Within another embodiment, the recovered thrombopoietin is concentrated by cation-exchange chromatography or ultrafiltration.

Within a related aspect, the present invention provides methods for isolating thrombopoietin (TPO) from a biological fluid. These methods comprise the steps of (a) reducing the volume of a TPO-containing biological fluid by a method selected from the group consisting of ligand affinity chromatography, ion-exchange chromatography, hydrophobic interaction chromatography and ultrafiltration to provide a concentrated fraction; (b) adjusting the salt concentration in the concentrated fraction to provide an adjusted solution; (c) acidifying the adjusted solution to precipitate contaminant proteins and provide a cleared solution; (d) fractionating the cleared solution by anion-exchange chromatography to provide a TPO-enriched fraction; (e) exposing the TPO-enriched fraction to hydroxyapatite whereby protein contaminants are bound to the hydroxyapatite and TPO remains substantially unbound; (f) recovering the unbound TPO; and (g) concentrating the recovered TPO by cation-exchange chromatography or ultrafiltration. Within one embodiment the biological fluid is cell-conditioned culture media or a fraction thereof. Within another embodiment the TPO is human TPO. Within yet another embodiment, the reducing step comprises direct capture by dye-ligand affinity chromatography, such as by direct capture on a matrix of derivatized, cross-linked agarose beads. Within a further embodiment the adjusting step comprises ultrafiltration. Within other embodiments the concentrating step comprises cation-exchange chromatography or anion-exchange chromatography.

Within a preferred embodiment of the invention the TPO recovered from the hydroxyapatite has a molecular weight of 70,000±10,000 daltons as determined by SDS-polyacrylamide gel electrophoresis under denaturing conditions, and is substantially free of low molecular weight (≦55 kD) protein contaminants and high molecular weight aggregates.

These and other aspects of the invention will become evident upon reference to the following detailed description.

DETAILED DESCRIPTION OF THE INVENTION

Prior to setting forth the invention in detail, it may be helpful to an understanding thereof to define certain terms used herein:

"Biological fluid" denotes any fluid derived from or containing cells, cell components or cell products. Biological fluids include, but are not limited to, cell culture supernatants, cell lysates, cleared cell lysates, cell extracts, tissue extracts, blood, plasma, serum, milk and fractions thereof.

"Cell-conditioned culture medium" denotes a nutrient medium in which cells have been cultured and which contains cell products.

The present invention provides methods for the purification of TPO from biological fluids, including cell-conditioned culture media. These methods are particularly advantageous in that they provide a homogeneous preparation of TPO that is substantially free of protein contaminants, including proteolytic degradation products and high molecular weight aggregates of TPO.

The methods of the present invention are useful for the preparation of human and non-human (e.g. murine, canine, porcine, bovine and ovine) thrombopoietins. These methods are particularly well suited to the purification of TPO from cell-conditioned culture media or fractions thereof (i.e. fractions of cell-conditioned culture media that have been previously enriched for TPO by other separation techniques). It is thus preferred to produce these thrombopoietins in genetically engineered, cultured cells according to methods generally known in the art. To summarize these methods, a DNA molecule encoding TPO is joined to other DNA sequences which provide for its maintenance and transcription in a host cell. The resulting expression vector is inserted into the host cell, and the resulting "transformed" cells are cultured in a suitable nutrient medium. It is preferred to engineer the cells to secrete the TPO into the medium, although TPO can be recovered from cell lysates and processed in vitro to yield active protein. See, in general, de Sauvage et al., *Nature* 369:533–538, 1994; Lok et al., *Nature* 369:565–568, 1994; Kaushansky et al., *Nature* 369:568–571, 1994; Wendling et al., *Nature* 369:571–574, 1994; Bartley et al., *Cell* 77:1117–1124, 1994; and co-pending, commonly assigned U.S. patent applications Ser. No. 08/366,859 and Ser. No. 08/347,029, which are incorporated herein by reference in their entirety.

TPO can also be produced by transgenic animals. When using transgenic animals it is particularly advantageous to produce heterologous proteins in their milk. Dairy animals such as cattle, sheep and goats are thus preferred hosts. See, for example, WIPO Publications WO 88/00239, WO 90/05188, WO 91/02318, and WO 92/11757; and U.S. Pat. Nos. 4,873,191; 4,873,316; and 5,304,489, which are incorporated herein by reference in their entirety.

The present invention is based in part on the discovery that a solution of thrombopoietin and protein contaminants can be efficiently fractionated by exposing the solution to hydroxyapatite. Protein contaminants, including high molecular weight aggregates of TPO, preferentially bind to the hydroxyapatite, while intact, biologically active thrombopoietin remains substantially unbound. The use of hydroxyapatite is advantageously combined with other purification and concentration techniques, including ion-exchange chromatography, ligand affinity chromatography, hydrophobic interaction chromatography, ultrafiltration, and differential precipitation.

It is preferred to concentrate and/or fractionate a complex, thrombopoietin-containing solution (e.g. cell-conditioned culture media) prior to exposing it to hydroxyapatite. Concentration can be acheived by such techniques as volume reduction using direct capture by ligand affinity chromatography, ion-exchange chromatography, hydrophobic interaction chromatography, ultrafiltration, or combinations of these techniques. Anion-exchange chromatography is a preferred method for fractionating (enriching) prior to exposing the solution to hydroxyapatite.

Within a preferred embodiment of the invention TPO is purified from a biological fluid containing TPO and protein contaminants in a series of steps beginning with reducing the volume of the fluid sample by ligand affinity chromatography, ion-exchange chromatography, hydrophobic interaction chromatography or ultrafiltration to provide a concentrated fraction having a reduced volume as compared to the starting material. The salt concentration in the concentrated fraction is then adjusted to provide an adjusted solution. Methods for adjusting the salt concentration include diafiltration, dilution, dialysis and hydrophobic interaction chromatography. The adjusted solution is then acidified to differentailly precipitate contaminant proteins, which are removed from the solution by filtration or other means. The resulting cleared solution is then fractionated by anion-exchange chromatography to provide a TPO-enriched fraction. Optionally, the pH may be adjusted to pH 5–9, preferably about pH 7–8, prior to anion-exchange chromatography. The TPO-enriched fraction is then combined with hydroxyapatite whereby protein contaminants are bound to the hydroxyapatite and the TPO remains substantially unbound. The unbound TPO is then collected and concentrated, such as by cation-exchange chromatography or ultrafiltration. Those skilled in the art will recognize that, with routine experimentation, the order of these steps can be varied. Buffer composition, ionic stregth, and pH will be adjusted as necessitated by the order of the steps and selection of specific techniques and fractionation media.

When working with biological fluids containing cells, cell debris, and the like it is preferred to first filter the fluid to remove these particulate contaminants.

As noted above, the volume reduction step can employ ligand affinity chromatography, ion-exchange chromatography, hydrophobic interaction chromatography or ultrafiltration. Volume reduction using direct capture by ligand affinity chromatography is preferred, and the use of dye-ligand affinity media is particularly preferred. Suitable dye-ligand affinity media include MIMETIC Red™ 2 A6XL, MIMETIC Red™ 3 A6XL, MIMETIC Blue™ 1 A6XL, MIMETIC Blue™ 2 A6XL, MIMETIC Orange™ 1 A6XL, MIMETIC Orange™ 2 A6XL, MIMETIC Orange™ 3 A6XL, MIMETIC Yellow™ 1 A6XL, MIMETIC Yellow™ 2 A6XL, and MIMETIC Green™ 1 A6XL (Affinity Chromatography Ltd., Freeport, Great Britain). These media are 6% cross-linked agarose beads, 45–164 µm, to which a dye ligand is linked via a spacer arm. It is particularly preferred to use MIMETIC Green™ 1 A6XL with a column size of 1.0 ml resin/300 ml sample volume. TPO binds to MIMETIC Green™ 1 A6XL, MIMETIC Blue™ 1 A6XL, MIMETIC Blue™ 2 A6XL, and MIMETIC Red™ 3 A6XL under physiological conditions (slightly alkaline pH and salt concentration of ≈150 mM), obviating the need to adjust pH and ionic strength of biological fluids prior to application to these media. The bound TPO can be eluted using increased salt concentration, increased pH, denaturing agents, or combinations thereof. For example, TPO bound to MIMETIC Green™ 1 A6XL can be eluted with 3M NaCl in 1% $NH_4OH$ or 4M guanidine. Other suitable dye-ligand affinity media include Blue Sepharose® (Pharmacia Biotech, Piscataway, N.J.) and the like. It is preferred to carry out this step in the cold (4°–10° C.) to minimize the likelihood of bacterial contamination. Methods for determining the binding specificity of dye-ligand affinity media and elution conditions suitable for TPO are known in the art and include the use of commercially available assay kits (e.g., PIKSI™ test kit available from Affinity Chromatography Ltd.). See, for example, Kroviarski et al, *J. Chromatoaraphy* 449:403–412, 1988 and Miribel et al., *J. Biochem. Biophys. Methods* 16:1–16, 1988.

Alternative methods for reducing the volume of the TPO-containing biological fluid can also be employed. Volume reduction can be achieved by capturing TPO on anion or cation-exchange media after appropriate adjustment of pH and conductivity of the fluid. After capture TPO can be eluted with a salt or pH gradient. In a second alternative TPO can be captured by hydrophobic interaction chromatography (HIC) after appropriate adjustment of the salt concentration of the fluid. TPO can be eluted from an HIC column with a low ionic strength buffer. Ultrafiltration can also be used to reduce volume. Various combinations of these methods can also be used.

The salt concentration of the concentrated fraction is then adjusted as required for subsequent fractionation. For example, fractionation by anion-exchange chromatography will typically require adjustment of the conductivity to about 3–6 mS/cm to avoid unacceptable losses. A preferred method of adjustment is buffer exchange by diafiltration. Other methods of adjusting the salt concentration include dilution to the desired conductivity and adjustment of pH, hydrophobic interaction chromatography, gel filtration, and reverse phase chromatography. Preferred HIC media include Phenyl Sepharose® (Pharmacia Biotech), Butyl Sepharose® (Pharmacia Biotech), and Fractogel® EMD Propyl 650(S) and Fractogel® EMD Phenyl 1 650(S), 20–40 μm (EM Science, Gibbstown, N.J.). Use of HIC will in general necessitate first increasing the conductivity of the enriched fraction by addition of salt. TPO is then eluted from HIC media using a low ionic strength buffer. If necessary, the ionic strength of the eluate is further adjusted prior to additional fractionation. Preferred gel filtration media include cross-linked beads of agarose, polyacrylamide or other polymers, such as Sephacryl® S-200 HR or S-300 HR (Pharmacia Biotech) and Superdex® (Pharmacia Biotech). Preferred reverse phase media include porous resins Oligo R2 and Oligo R3 (PerSeptive Biosystems, Inc., Framingham, Mass.).

Contaminating proteins can be removed from the resulting adjusted solution by mild acid precipitation and filtration. When using diafiltration in the adjusting step it is convenient to use an acidic exchange buffer (e.g. 25 mM sodium acetate buffer, pH 5.0), thereby combining the adjustment of salt concentration and differential precipitation of contaminants.

Anion-exchange chromatography is carried out using media that in general comprise an insoluble, particulate support derivatized with tertiary or quaternary amine groups. Suitable supports in this regard include agarose beads, dextran beads, polystyrene beads and the like. Supports derivatized with trimethylaminoethyl groups are preferred. Suitable anion-exchange media include Macro-Prep® Q (Bio-Rad Laboratories, Hercules, Calif.), Q-HyperD™ (BioSepra, Inc., Marlborough, Mass.), Q Sepharose® (Pharmacia), and the like. A particularly preferred anion-exchanger is Fractogel® EMD TMAE-650(S) (EM Science, Gibbstown, N.J.). Anion-exchange chromatography is typically carried out at a pH of 5–9, preferably 6.5–8.0, in Tris or phosphate buffer, and at a temperature of about 18°–25° C., preferably about 20° C. (room temperature). The preferred column size is 1.0 ml resin per 20–30 mg total protein.

The eluate from the anion-exchange column is then exposed to hydroxyapatite so that protein contaminants are bound to the hydroxyapatite and the TPO remains substantially unbound. Within a preferred procedure, hydroxyapatite is prepared in the form of a column, using 1.0 ml resin/4.0–8.0 mg of total protein in the sample. The column is equilibrated with a low ionic strength buffer at slightly acidic to near-neutral pH, such as 10 mM sodium phosphate buffer at pH 5.5–7.5. The conductivity of the eluate fraction from the anion-exchange step is adjusted to about 10–30 mS/cm, preferably about 11 mS/cm, the solution is applied to the column at room temperature, and the flow-through fraction, which contains TPO, is collected.

The flow-through fraction containing the unbound TPO is then concentrated. Suitable methods of concentration include cation-exchange chromatography and ultrafiltration. Cation-exchange chromatography is carried out using media that in general comprise an insoluble, particulate support derivatized with sulfopropyl or carboxymethyl groups. Suitable supports in this regard include beaded, cross-linked agarose, acrylamide, methacrylate, and the like. Supports derivatized with sulfopropyl groups are preferred. Commercially available cation-exchange media of this type include S-HyperD™ (BioSepra), TSK-Gel® S (TosoHaas, Montgomeryville, Pa.), SP Sepharose® (Pharmacia Biotech), and the like. A particularly preferred sulfopropyl-derivatized medium is Fractogel® EMD $SO_3^-$-650(S) (EM Science). In a typical procedure, a TPO-containing solution having an acidic pH (e.g., 4.0–5.0) and low ionic strength (e.g., 3–6 mS/cm) is applied to a column of Fractogel® EMD $SO_3^-$-650 (S), using 1.0 ml resin/3.0–6.0 mg total protein (by $A_{280}$) at room temperature. The column is washed to remove unbound material, and TPO is eluted with a higher ionic strength buffer (e.g., 0.1–0.5M NaCl at pH 6–9). A preferred elution buffer is 40 mM Na phosphate buffer, pH 9, containing 0.28M NaCl.

Although the procedure described above and in the following experimental example utilizes column chromatography, those skilled in the art will recognize that batch processing can also be utilized.

Thrombopoietin prepared according to the present invention can be used therapeutically wherever it is desirable to increase proliferation of cells in the bone marrow, such as in the treatment of cytopenias, such as that induced by aplastic anemia, myelodisplastic syndromes, chemotherapy or congenital cytopenias. TPO is particularly useful for increasing platelet production, such as in the treatment of thrombocytopenia. Thrombocytopenia is associated with a diverse group of diseases and clinical situations that may act alone or in concert to produce the condition. Lowered platelet counts can result from, for example, defects in platelet production, abnormal platelet distribution, dilutional losses due to massive transfusions, or abnormal destruction of platelets. For example, chemotherapeutic drugs used in cancer therapy may suppress development of platelet progenitor cells in the bone marrow, and the resulting thrombocytopenia limits the chemotherapy and may necessitate transfusions. In addition, certain malignancies can impair platelet production and platelet distribution. Radiation therapy used to kill malignant cells also kills platelet progenitor cells. Thrombocytopenia may also arise from various platelet autoimmune disorders induced by drugs, neonatal alloimmunity or platelet transfusion alloimmunity. TPO can reduce or eliminate the need for transfusions, thereby reducing the incidence of platelet alloimmunity. Abnormal destruction of platelets can result from: (1) increased platelet consumption in vascular grafts or traumatized tissue; or (2) immune mechanisms associated with, for example, drug-induced thrombocytopenia, idiopathic thrombocytopenic purpura (ITP), autoimmune diseases, hematologic disorders such as leukemia and lymphoma or metastatic cancers involving bone marrow. Other indications for TPO include aplastic anemia and drug-induced marrow suppression resulting from, for example, chemotherapy or treatment of HIV infection with AZT.

Thrombocytopenia is manifested as increased bleeding, such as mucosal bleedings from the nasal-oral area or the gastrointestinal tract, as well as oozing from wounds, ulcers or injection sites.

For pharmaceutical use, TPO is formulated for parenteral, particularly intravenous or subcutaneous, delivery according to conventional methods. Intravenous administration will be by bolus injection or infusion over a typical period of one to several hours. In general, pharmaceutical formulations will include TPO in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. In addition, TPO may be combined with other cytokines, particularly early-acting cytokines such as stem cell factor, IL-3, IL-6, IL-11 or GM-CSF. When utilizing such a combination therapy, the cytokines may be combined in a single formulation or may be administered in separate formulations. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses will generally be in the range of 0.1 to 100 µg/kg of patient weight per day, preferably 0.5–20 µg/kg per day, with the exact dose determined by the clinician according to accepted standards, taking into account the nature and severity of the condition to be treated, patient traits, etc. Determination of dose is within the level of ordinary skill in the art. TPO will commonly be administered over a period of up to 28 days following chemotherapy or bone-narrow transplant or until a platelet count of >20,000/mm$^3$, preferably >50,000/mm$^3$, is achieved. More commonly, TPO will be administered over one week or less, often over a period of one to three days. In general, a therapeutically effective amount of TPO is an amount sufficient to produce a clinically significant increase in the proliferation and/or differentiation of lymphoid or myeloid progenitor cells, which will be manifested as an increase in circulating levels of mature cells (e.g. platelets or neutrophils). Treatment of platelet disorders will thus be continued until a platelet count of at least 20,000/mm$^3$, preferably 50,000/mm$^3$, is reached. TPO can also be administered in combination with other cytokines such as IL-3, -6 and -11; stem cell factor; erythropoietin (EPO); G-CSF and GM-CSF. Within regimens of combination therapy, daily doses of other cytokines will in general be: EPO, ≦150 U/kg; GM-CSF, 5–15 µg/kg; IL-3, 1–5 µg/kg; and G-CSF, 1–25 µg/kg. Combination therapy with EPO, for example, is indicated in anemic patients with low EPO levels.

TPO is also a valuable tool for the in vitro study of the differentiation and development of hematopoietic cells, such as for elucidating the mechanisms of cell differentiation and for determining the lineages of mature cells, and may also find utility as a proliferative agent in cell culture.

TPO can also be used ex vivo, such as in autologous marrow culture. Briefly, bone marrow is removed from a patient prior to chemotherapy and treated with TPO, optionally in combination with one or more other cytokines. The treated marrow is then returned to the patient after chemotherapy to speed the recovery of the marrow. In addition, TPO can be used for the ex vivo expansion of marrow or peripheral blood progenitor (PBPC) cells. Prior to chemotherapy treatment, marrow can be stimulated with stem cell factor (SCF) or G-CSF to release early progenitor cells into peripheral circulation. These progenitors can be collected and concentrated from peripheral blood and then treated in culture with TPO, optionally in combination with one or more other cytokines, including but not limited to SCF, G-CSF, IL-3, GM-CSF, IL-6 or IL-11, to differentiate and proliferate into high-density megakaryocyte cultures, which can then be returned to the patient following high-dose chemotherapy.

The invention is further illustrated by the following non-limiting examples.

EXAMPLES

Example 1

A column of MIMETIC Green™ 1 A6XL (Affinity Chromatography Ltd., Freeport, Great Britain) (9 cm diameter× 12 cm high) was prepared. Column operation was carried out at 4° C. The column was equilibrated using 5 column volumes of phosphate buffered saline (PBS; 120 mM NaCl, 2.7 mM KCl, 10 mM phosphate, pH 7.2) at a flow rate of 1 cm/minute.

Two hundred liters of cell culture medium conditioned by baby hamster kidney cells transfected with a human TPO expression vector and containing TPO was filtered through a 0.22 µAm cellulose acetate or polysufon membrane filter. The filtered medium was loaded onto the column at a rate of 1 cm/minute. The column was washed with 5 column volumes of PBS or until the absorbance (280 nm) reached baseline. Bound protein was eluted from the column using a solution of 1% ammonium hydroxide, 3M NaCl. Protein content of the column eluate was monitored by absorbance at 280 nm. Peak fractions were collected. The protein peak typically eluted in about 2 column volumes.

The elution peak was allowed to stand at 4° C. for 15 minutes, then the pH was adjusted to 5.0 with 50% acetic acid. A milky white precipitate formed, which was stored at −80° C. in the eluate.

The column was cleaned using 3 column volumes of 1.0M NaOH. The NaOH was left on the resin for 2 hours, then the resin was washed with 5 volumes of water and stored in 20% ethanol.

700 liters of conditioned media (starting volume) was processed in four batches through the MIMETIC Green™ column, then the eluted material was pooled. This pool contained approximately six grams of total protein.

The eluate/precipitate from the MIMETIC Green™ column (approximately 2 liter volume) was thawed overnight at room temperature, then filtered through a 155 cm$^2$, 3 µm polyurethane membrane capsule filter (#12116 pleated capsule, Gelman Sciences, Ann Arbor, Mich.) to remove any precipitate. When filtration was complete, the capsule was washed with 300 ml of 25 mM sodium acetate, pH 5.0.

The salt concentration of the clear filtrate was adjusted by ultrafiltration using a diafiltration hollow fiber membrane (30,000 molecular weight cutoff) from AG/Technology (Needham, Mass.) and a housing size 6 (0.28 m$^2$ area; #UFP-30-E-6A from AG/Technology). The exchange buffer was 25 mM Na acetate, pH 5.0. Filtrate flux rate was about 60 ml/minute at 20 psi. The material became cloudy after about three volumes of diafiltration. After about 7 volumes, the conductivty reached about 4 mS/cm. The pH was 5.0, and the material had a milky-white, turbid appearance. This material was stored overnight at 4° C.

The diafiltration unit was cleaned by flushing with water, circulating 0.5M NaOH through the system for one hour, and flushing again with water. The system was stored in 20% ethanol or 0.1M NaOH.

The diafiltered material was adjusted to 20 mM Tris with 1M Tris pH 8.0, and the pH of the resulting solution was adjusted to 8.0 with 2M NaOH. The solution was then filtered through a 0.45 μm polyurethane membrane capsule filter (#12131 Versaflow™ capsule; Gelman Sciences, Ann Arbor, Mich.).

The filtered material was then fractionated by anion-exchange chromatography on a 9 cm diameter×11 cm high column of Fractogel® EMD TMAE-650(S) (approximately 700 ml of resin) having a particle size of 0.025–0.04 mm (EM Science). The column was first equilibrated with 3 column volumes of 20 mM Tris, pH 8.0. The protein solution was loaded onto the column at a linear velocity of 1 cm/minute. The loaded column was washed with 3 column volumes of 20 mM Tris, pH 8.0, then bound protein was eluted with 10 column volumes of a 0–0.3M NaCl gradient in 20 mM Tris pH 8.0, followed by two column volumes of 0.3M NaCl in 20 mM Tris pH 8.0. TPO began to elute from the column at about 30 mM NaCl.

The Fractogel® column was cleaned with 3 column volumes of 1M NaCl in 20 mM Tris pH 8.0 and sanitized with 3 column volumes of 0.5M NaOH, then allowed to stand in 0.5M NaOH for two hours. The column was then washed with 5 volumes of water and stored in 20% ethanol.

Fractions from the column were analyzed by Western blot analysis after electrophoresis on a 10–20% gradient polyacrylamide gel (Novex, San Diego, Calif.) under reducing conditions. Fractions of 70 kD material showing positive in the Western blot were pooled.

Protein content of the TMAE eluate was quantitated by measuring the absorbance at 280 nm. The eluate was adjusted to 10 mM Na phosphate with 0.5M Na phosphate pH 6.8, and the pH of this solution was adjusted to 6.8 with 2N NaOH. Conductivity was adjusted to 10 mS/cm by dilution with water (approximately two-fold dilution), and the pH was readjusted to 6.8 as necessary.

The diluted eluate was then run through a column of ceramic hydroxyapatite (Macro-Prep® Ceramic Hydroxyapatite, 40 μm; Bio-Rad Laboratories, Hercules, Calif.) using approximately 1 ml of resin per 6 mg of total protein. 700 liters of conditioned medium processed to this point contained about 900 mg of protein, which was processed on 150 ml of resin (column size of 4.4 cm diameter× 15 cm). The column was equilibrated with 10 mM Na phosphate pH 6.8, then loaded at a rate of 1.5 cm/minute. The flow-through fraction was collected. The column was then washed with 4 column volumes of 10 mM Na phosphate pH 6.8, and the first column volume of the wash was combined with the flow-through fraction. Remaining contaminants and residual TPO (about 10–20% of total TPO) were washed from the column with 0.5M Na phosphate pH 6.8. The column was sanitized with 3 column volumes of 0.5M NaOH, and the column was allowed to stand in the NaOH for 2 hours, after which it was washed with 5 column volumes of water. The column was then stored in 20% ethanol.

The product stream before and after purification on hydroxyapatite was analyzed by reverse-phase HPLC using a C-18 column and an acetonitrile gradient. Results indicated that essentially all impurities present in the TMAE eluate pool were bound to the hydroxyapatite. The flow-through fraction from the hydroxyapatite column contained a single peak by HPLC.

The TPO-containing fraction from the hydroxyapatite column contained about 250 mg total protein by $A_{280}$. This material was adjusted to 20 mM Na acetate by addition of powdered Na acetate, pH was adjusted to 5.0, and the solution was diluted with water to a conductivity of 6 mS/cm.

A 3.2 cm diameter×3.7 cm column containing approximately 30 ml of Fractogel® EMD $SO_3^-$-650(S) (EM Science) was equilibrated with 3 column volumes of 20 mM Na acetate, pH 5.0. The TPO solution was loaded onto the column at a flow rate of 2 cm/minute. The column was washed with 5 column volumes of 20 mM Na acetate, pH 5.0. TPO was eluted from the column with 20 mM Na acetate pH 5.0 containing 0.5M NaCl. The protein concentration of the eluate was approximately 1 mg/ml.

The column was cleaned with 3 column volumes of 0.5M NaOH and allowed to stand in NaOH for two hours, then washed with 5 column volumes of water and stored in 20% ethanol.

Example 2

Human TPO prepared essentially as disclosed in Example 1 was analyzed by electrophoresis on 4–20% Tris-glycine gels (obtained from Novex, San Diego, Calif.) followed by silver staining or western blotting. One μg of protein was electorphoresed under reducing conditions, and the gel was stained with Coommassie blue and destained, followed by staining with a Daiichi silver stain kit (Integrated Separation Systems, Natick, Mass.). With this heavy gel loading, a single, dark, broad band was centered at Mr≈70 kD. 100 ng of protein was electrophoresed under non-reducing conditions and transferred to a nitrocellulose membrane. The blot was probed with a cocktail of anti-TPO monoclonal antibodies, followed by horseradish peroxidase-conjugated goat anti-mouse antibody and ECL™ detection reagents (Amersham Corp.). The blot was then exposed to X-ray film. A broad band was present centered at about 70 kD. Several much fainter bands beginning at just under 250 kD were also detected.

Biological activity of TPO was assayed in a mitogenesis assay using BaF3 cells transfected with an expression vector encoding the human MPL receptor (Vigon et al., *Proc. Natl. Acad. Sci. USA* 89:5640–5644, 1992) as target cells. BaF3 is an interleukin-3 dependent prelymphoid cell line derived from murine bone marrow (Palacios and Steinmetz, *Cell* 41:727–734, 1985; Mathey-Prevot et al., *Mol. Cell. Biol.* 6:4133–4135, 1986). Cells were exposed to test samples in the presence of $^3$H-thymidine. The amount of $^3$H-thymidine incorporated into cellular DNA was quantitated by comparison to a standard curve of human TPO. The preparation was found to have an activity of $1.77 \times 10^6$ units/ml, wherein 10 U/ml is defined as the amount giving half-maximal stimulation in the mitogenesis assay. By amino acid analysis, the protein concentration in the preparation was 0.41 mg/ml, giving a specific activity of $4.32 \times 10^6$ U/mg.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for purifying human thrombopoietin (TPO) from a biological fluid comprising:

reducing the volume of a human TPO-containing biological fluid by a method selected from the group consisting of ligand affinity chromatography, ion-exchange chromatography, hydrophobic interaction chromatography and ultrafiltration to provide a concentrated fraction;

adjusting the salt concentration of the concentrated fraction to provide an adjusted solution;

acidifying the adjusted solution to precipitate contaminant proteins and provide a cleared solution;

fractionating the cleared solution by anion-exchange chromatography to provide a TPO-enriched fraction;

exposing the TPO-enriched fraction to hydroxyapatite whereby protein contaminants are bound to the hydroxyapatite and TPO remains substantially unbound;

collecting the unbound TPO; and concentrating the collected TPO by cation-exchange chromatography or ultrafiltration.

2. A method according to claim 1 wherein the biological fluid is cell-conditioned culture media or a fraction thereof.

3. A method according to claim 1 wherein the reducing step comprises direct capture by dye-ligand affinity chromatography.

4. A method according to claim 3 wherein the reducing step comprises direct capture on a matrix of derivatized, cross-linked agarose beads.

5. A method according to claim 1 wherein the adjusting step comprises ultrafiltration.

6. A method according to claim 1 wherein the concentrating step comprises cation-exchange chromatography.

7. A method according to claim 6 wherein the concentrating step employs an insoluble support derivatized with sulfopropyl groups.

8. A method according to claim 1 wherein the fractionating step employs an insoluble support derivatized with trimethylaminoethyl groups.

9. A method according to claim 1 wherein the collected TPO has a molecular weight of 70,000±10,000 daltons as determined by SDS-polyacrylamide gel electrophoresis under denaturing conditions.

10. A method according to claim 1 wherein said protein contaminants comprise aggregates of thrombopoietin.

11. A method for purifying human thrombopoietin (TPO) from a biological fluid comprising:

reducing the volume of a human TPO-containing biological fluid by direct capture by dye-ligand affinity chromatography to provide a concentrated fraction;

adjusting the salt concentration in the concentrated fraction by ultrafiltration to provide an adjusted solution;

fractionating the adjusted solution by anion-exchange chromatography to provide a TPO-enriched fraction;

exposing the TPO-enriched fraction to hydroxyapatite whereby protein contaminants bind to the hydroxyapatite and TPO is eluted; and concentrating the eluted TPO by cation-exchange chromatography.

12. A method for removing protein contaminants from a solution comprising human thrombopoietin and protein contaminants comprising exposing the solution to hydroxyapatite, whereby said protein contaminants are bound to said hydroxyapatite and said thrombopoietin remains substantially unbound, and recovering unbound thrombopoietin.

13. A method according to claim 12 wherein said protein contaminants comprise aggregates of thrombopoietin.

14. A method according to claim 12 wherein said solution is prepared by fractionating a thrombopoietin-containing liquid composition by ion-exchange chromatography, ligand affinity chromatography or hydrophobic interaction chromatography.

15. A method according to claim 14 wherein said solution is prepared by fractionating a thrombopoietin-containing liquid composition by anion-exchange chromatography.

16. A method according to claim 14 wherein said solution is prepared by fractionating a thrombopoietin-containing liquid composition by a combination of anion-exchange chromatography and ligand affinity chromatography.

17. A method according to claim 12 wherein the recovered thrombopoietin is concentrated by cation-exchange chromatography or ultrafiltration.

18. A method according to claim 11 wherein the eluted TPO has a molecular weight of 70,000±10,000 daltons as determined by SDS-polyacrylamide gel electrophoresis under denaturing conditions.

19. A method according to claim 12 wherein the recovered, unbound thrombopoietin has a molecular weight of 70,000±10,000 daltons as determined by SDS-polyacrylamide gel electrophoresis under denaturing conditions.

* * * * *